(12) United States Patent
Shi et al.

(10) Patent No.: US 10,952,669 B2
(45) Date of Patent: Mar. 23, 2021

(54) SYSTEM FOR MONITORING EATING HABIT USING A WEARABLE DEVICE

(71) Applicant: International Business Machines Corporation, Armonk, NY (US)

(72) Inventors: Conglei Shi, Yorktown Heights, NY (US); Yinglong Xia, Rye Brook, NY (US); Jui-Hsin Lai, White Plains, NY (US); Yu Ma, White Plains, NY (US)

(73) Assignee: International Business Machines Corporation, Armonk, NY (US)

(*) Notice: Subject to any disclaimer, the term of this patent is extended or adjusted under 35 U.S.C. 154(b) by 383 days.

(21) Appl. No.: 15/853,082

(22) Filed: Dec. 22, 2017

(65) Prior Publication Data

US 2019/0192073 A1 Jun. 27, 2019

(51) Int. Cl.
*G06K 9/00* (2006.01)
*A61B 5/00* (2006.01)
*G09B 19/00* (2006.01)
*A61B 5/0488* (2006.01)
*A61B 5/11* (2006.01)
(Continued)

(52) U.S. Cl.
CPC .......... *A61B 5/4866* (2013.01); *A61B 5/0013* (2013.01); *A61B 5/0077* (2013.01); *A61B 5/04012* (2013.01); *A61B 5/0488* (2013.01); *A61B 5/1128* (2013.01); *G06F 1/163* (2013.01); *G06N 20/00* (2019.01); *G09B 19/0092* (2013.01); *A61B 5/04884* (2013.01); *A61B 5/4205* (2013.01); *A61B 5/4542* (2013.01);
(Continued)

(58) Field of Classification Search
None
See application file for complete search history.

(56) References Cited

U.S. PATENT DOCUMENTS

2014/0194702 A1 7/2014 Tran
2014/0273858 A1 9/2014 Panther et al.
(Continued)

OTHER PUBLICATIONS

Qianyi Huang ; Wei Wang ; Qian Zhang, Your Glasses Know Your Diet: Dietary Monitoring Using Electromyography Sensors, Jan. 20, 2017, IEEE Internet of Things Journal ( vol. 4 , Issue: 3 , Jun. 2017 ), pp. 705-712 (Year: 2017).*

(Continued)

*Primary Examiner* — Atiba O Fitzpatrick
(74) *Attorney, Agent, or Firm* — Patterson + Sheridan, LLP

(57) ABSTRACT

Method and apparatus for monitoring eating behavior are disclosed. A wearable device including an imaging sensor, an electromyography (EMG) sensor, and a processing unit is configured to collect EMG data via the EMG sensor, transmit the EMG data to a computing device, receive a control signal to capture one or more images via the imaging sensor, capture, one or more images, and transmit the one or more images. A computing device is disclosed including a processor and a memory containing a machine learning model and computer program code that, when executed, performs an operation. The operation includes receiving EMG data, processing the EMG data as input to a trained machine learning model, transmitting the control signal to capture one or more images via the imaging sensor, receiving the one or more images, and determining nutritional content of the food or beverage using the one or more images.

20 Claims, 7 Drawing Sheets

(51) Int. Cl.
  *G06F 1/16*    (2006.01)
  *A61B 5/04*    (2006.01)
  *G06N 20/00*   (2019.01)
  *G02C 11/00*   (2006.01)

(52) U.S. Cl.
  CPC .......... *A61B 5/6803* (2013.01); *A61B 5/7267* (2013.01); *G02C 11/10* (2013.01)

(56) References Cited

U.S. PATENT DOCUMENTS

| | | |
|---|---|---|
| 2015/0126873 A1 | 5/2015 | Connor |
| 2015/0294450 A1 | 10/2015 | Eyring |
| 2015/0313539 A1 | 11/2015 | Connor |
| 2015/0379238 A1 | 12/2015 | Connor |
| 2016/0012749 A1 | 1/2016 | Connor |
| 2016/0029951 A1 | 2/2016 | Dunki-Jacobs et al. |
| 2016/0350514 A1 | 12/2016 | Rajendran et al. |
| 2017/0220772 A1 | 8/2017 | Vleugels et al. |
| 2018/0242908 A1 | 8/2018 | Sazonov et al. |

OTHER PUBLICATIONS

Yin et al.; Ttl: AutoDietary: A Wearable Acoustic Sensor System for Food Intake Recognition in Daily Life; Publication Ttl: IEEE Sensors Journal, vol. 16, No. 3, pp. 806-816; 2016; Publisher: IEEE; Country of Publication: USA; ISSN:1530-437X; Database: INSPEC.

* cited by examiner

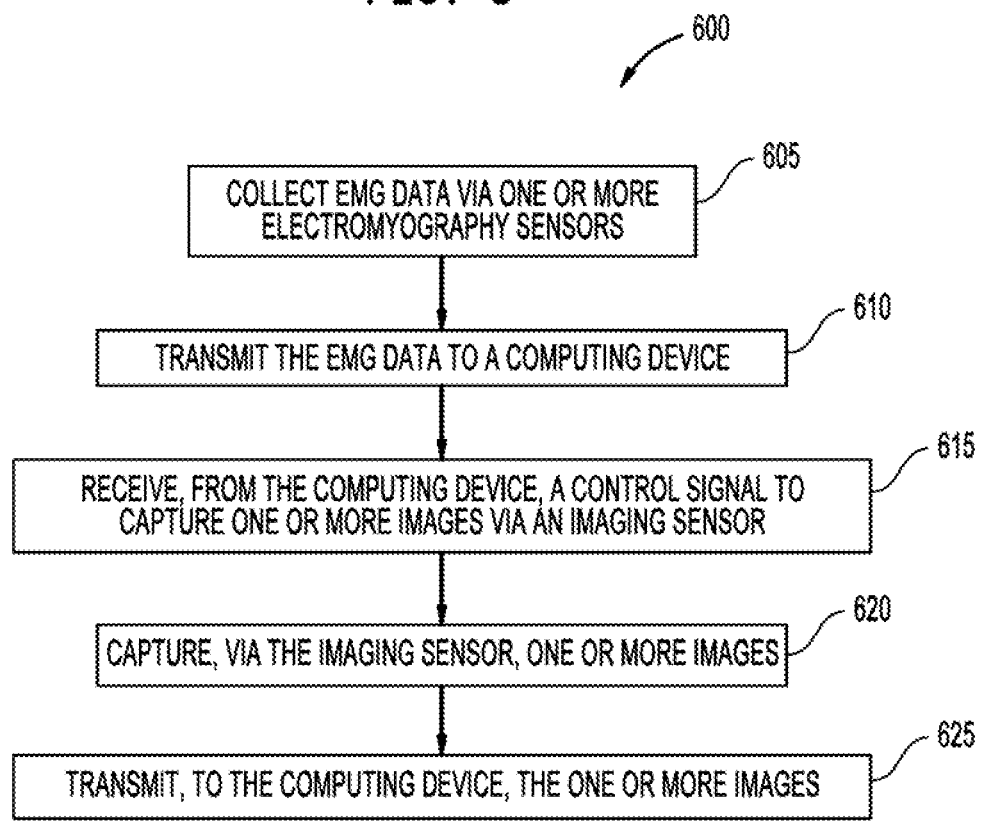

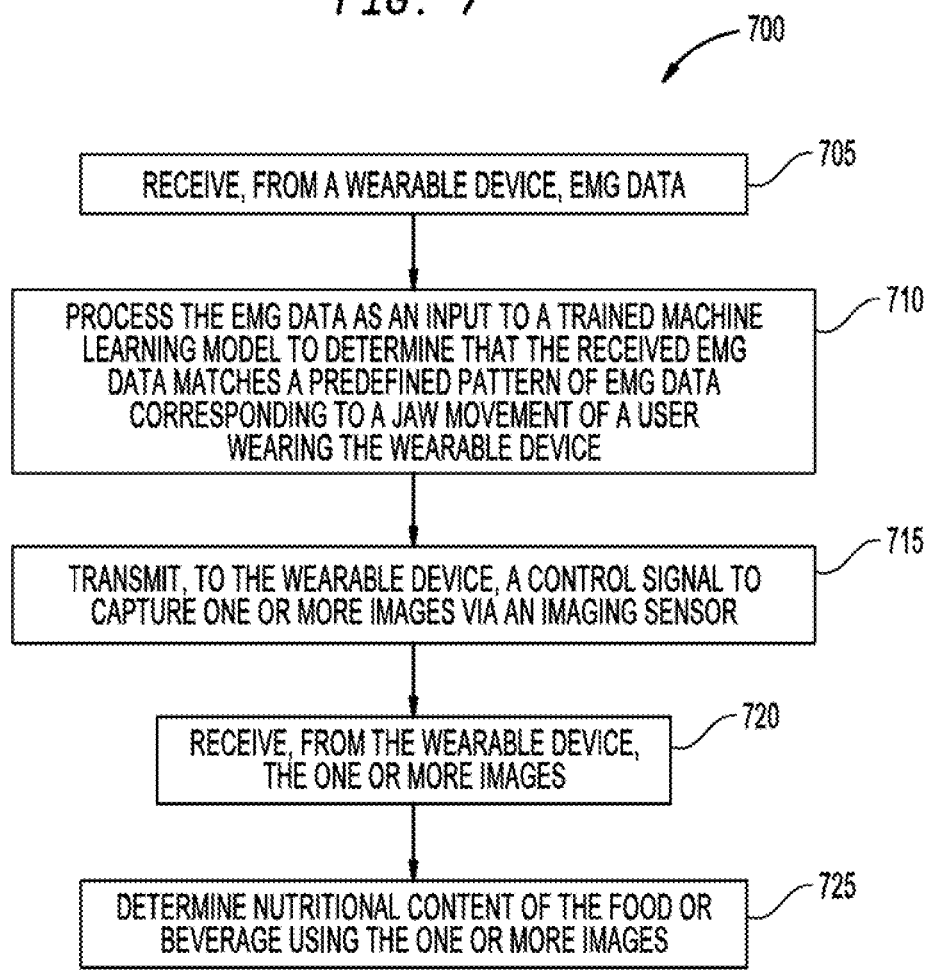

SYSTEM FOR MONITORING EATING HABIT USING A WEARABLE DEVICE

BACKGROUND

The present invention relates to wearable devices, and more specifically, to utilizing machine learning in conjunction with wearable devices to monitor eating habits of a user.

Wearable devices have become extremely popular, and a wide variety of wearable devices now exist, including smart watches or wristbands, smart glasses, and the like. Ingestible and implantable devices can often be used in many similar applications. Depending on the desired use, wearable devices can monitor and record various types of data about the user. This data can include fitness information, such as a number of steps taken. Additionally, the monitored data can include biometric data of the user, such as the heartrate, in order to facilitate the use of wearable devices in health-related settings. For example, wearables can be used to aide with weight loss, treat weight disorders, stimulate the gastrointestinal tract of the user, observe sleep patterns, and track physical exercise activities of the user.

In order to control their weight, many people monitor their eating habits to ensure they do not consume excessive food or beverages. However, these approaches require the user to manually track their consumption, which is time consuming and easy to forget. Further, existing methods are prone to inaccuracy, as users do not know the nutritional content of most foods, and tend to underestimate how much they have consumed. There is a need for an integrated device that allows for improved monitoring of eating habits.

SUMMARY

According to one embodiment of the present disclosure, a system comprising a computing device and a wearable device is disclosed. The computing device includes a processor and a memory containing a machine learning model and computer program code that, when executed, performs an operation. The wearable device includes an imaging sensor, one or more electromyography (EMG) sensors, and a processing unit. The processing unit of the wearable device is configured to collect EMG data via the one or more electromyography sensors of the wearable device, transmit the EMG data to the computing device, receive, from the computing device, a control signal to capture one or more images via the imaging sensor, capture, via the imaging sensor, one or more images, and transmit, to the computing device, the one or more images. Further, the operation performed by execution of the computer program code of the computing device comprises receiving, from the wearable device, the EMG data and processing the EMG data as an input to a trained machine learning model to determine that the received EMG data matches a predefined pattern of EMG data corresponding to a jaw movement of a user wearing the wearable device. The operation also includes transmitting, to the wearable device, the control signal to capture one or more images via the imaging sensor, receiving, from the wearable device, the one or more images, and determining nutritional content of the food or beverage using the one or more images.

According to a second embodiment of the present disclosure, a method is disclosed. The method includes receiving electromyography (EMG) data from a wearable device, where the EMG data represents jaw movement of a first user wearing the wearable device, and processing the received EMG data using a first machine learning model to determine that the user is consuming food. The method also includes transmitting a control signal to the wearable device, wherein the control signal instructs the wearable device to capture one or more images using an imaging sensor of the wearable device, receiving the one or more images from the wearable device, and determining nutritional content of the food using the one or more images.

According to a third embodiment of the present disclosure, a computer-readable storage medium having computer-readable program code embodied therewith is disclosed. The computer-readable program code is executable by one or more computer processors to perform an operation including receiving, from a wearable device, electromyography (EMG) data about jaw movement of a user. The operation also includes determining that the user is consuming food or beverages by processing the EMG data using a first trained machine learning model and transmitting, to the wearable device, an instruction to capture one or more images. The operation further includes receiving, from the wearable device, the one or more images, and determining nutritional content of the food or beverage using the one or more image.

BRIEF DESCRIPTION OF THE SEVERAL VIEWS OF THE DRAWINGS

FIG. 6 is a flow diagram illustrating a method for monitoring eating habits, according to one embodiment of the present disclosure.

FIG. 7 is a flow diagram illustrating a method for monitoring eating habits, according to one embodiment of the present disclosure.

DETAILED DESCRIPTION

Users who wish to track their eating habits are usually forced to do so manually, which is time-consuming and inaccurate. Further, existing solutions that attempt to enable automatic tracking are insufficient in a variety of ways. Embodiments of the present disclosure present an integrated device that allows users to automatically monitor their consumption using intelligent machine learning models that can be constantly refined, without sacrificing privacy or accuracy. Embodiments of the present disclosure present several significant advantages over existing solutions. According to one embodiment, an imaging device, such as a camera, is used to capture images of food and drinks being consumed, and a biometric sensor, such as an electromyography (EMG) sensor, is used to automatically detect when the user is consuming food. In an embodiment, the biometric sensor and imaging sensor are integrated in a single wearable device, which reduces the complexity of the system for users who do not want to use multiple devices to monitor their habits.

Utilizing a camera on a wearable device can introduce privacy concerns for many users who do not want everything they do being recorded. Embodiments of the present solution include an imaging sensor that is configured to record images only when consumption of food is detected via the biometric sensor. This allows increased privacy, without sacrificing accuracy. In an embodiment, detection of the consumption of food or beverages is achieved utilizing machine learning models, which allows for accurate and reliable determinations. Further, in an embodiment, the one or more machine learning models can be refined using the user's own data, which increases the accuracy as compared to a more generic one-size-fits-all approach. Notably, embodiments of the present disclosure present an imaging sensor and a biometric sensor integrated into a single wearable device, so as to reduce complexity and increase the likelihood a user will use the device.

Figure 1:
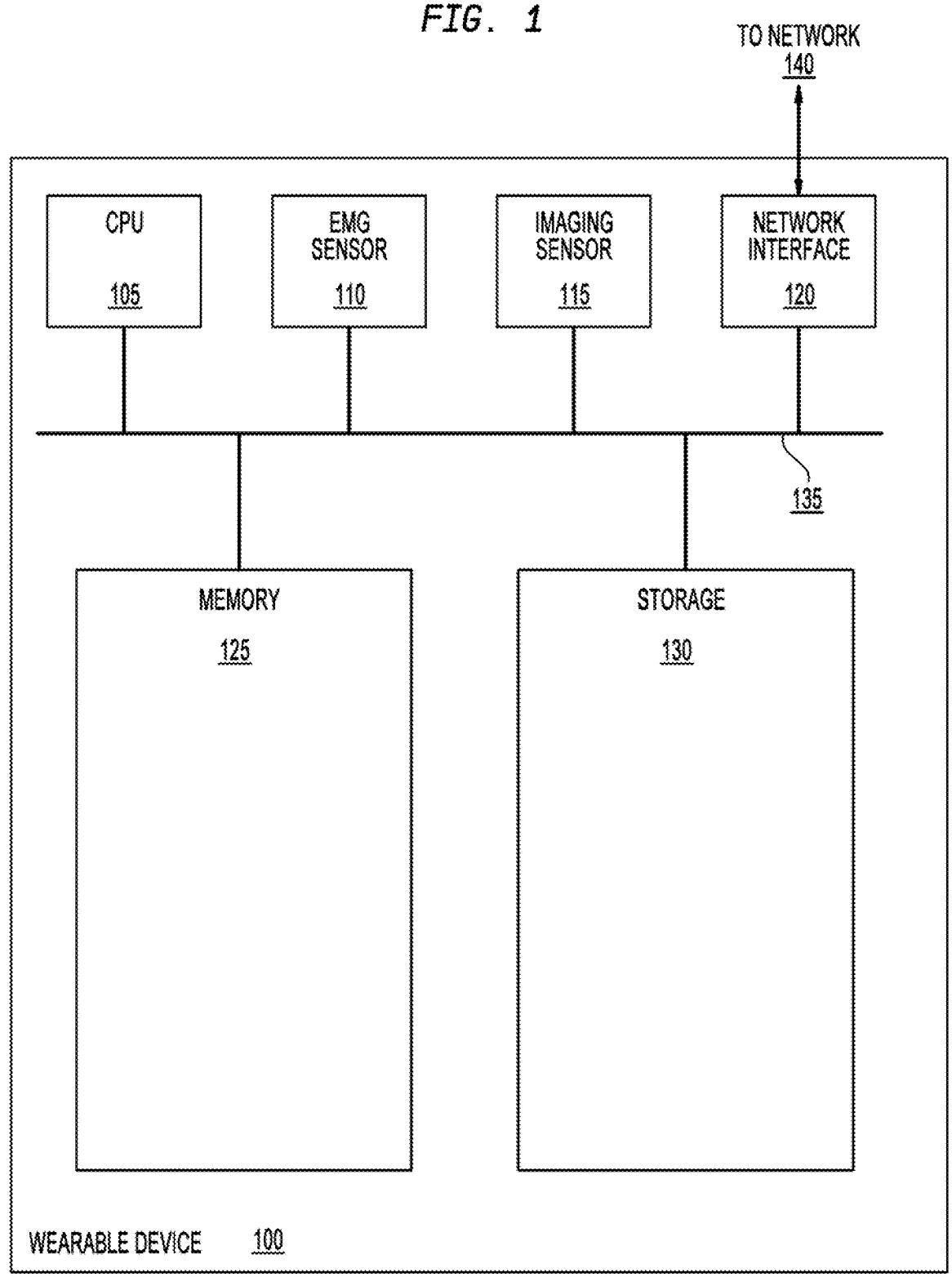
FIG. 1 is a block diagram illustrating a wearable device, according to one embodiment of the present disclosure.

FIG. 1 is a block diagram illustrating a Wearable Device 100, according to one embodiment of the present disclosure. For example, in an embodiment the Wearable Device 100 is a glasses-based device. As illustrated, Wearable Device 100 includes a CPU 105, an EMG sensor 110, an Imaging Sensor 115, a Network Interface 120, a Memory 125, and a Storage 130, each connected via a bus or interconnect 135. In some embodiments, the Wearable Device 100 may include an I/O device interface connecting I/O devices (e.g., keyboard, display and mouse devices) to the Wearable Device 100.

The CPU 105 is configured to retrieve and execute programming instructions stored in the memory 125 and storage 130. Similarly, the CPU 105 is configured to store and retrieve application data residing in the memory 125 and storage 130. The interconnect 135 is configured to move data, such as programming instructions and application data, between the CPU 105, storage unit 130, network interface 120, memory 125, EMG Sensor 110, and Imaging Sensor 115. The CPU 105 is included to be representative of a single CPU, multiple CPUs, a single CPU having multiple processing cores, and the like. Memory 125 is generally included to be representative of a random access memory. The network interface 120 is configured to transmit data via the communications network 140. Although shown as a single unit, the storage 130 may be a combination of fixed and/or removable storage devices, such as fixed disc drives, removable memory cards, optical storage, SSD or flash memory devices, network attached storage (NAS), or connections to storage area-network (SAN) devices.

In some embodiments, Wearable Device 100 does not have separate Storage 130 and Memory 125. For example, to reduce manufacturing costs, Wearable Device 100 may be configured with a single memory component, or with only hardcoded memory. In an embodiment, Network 140 is a personal area network, such as a Bluetooth connection. In some embodiments, Network 140 is a local area network or wide area network, such as the Internet. As will be discussed below in more detail, the illustrated Wearable Device 100 is generally configured to monitor EMG data from a user using EMG sensor 110 and capture images using Imaging Sensor 115, and transmit and receive data using Network Interface 120.

Figure 2:
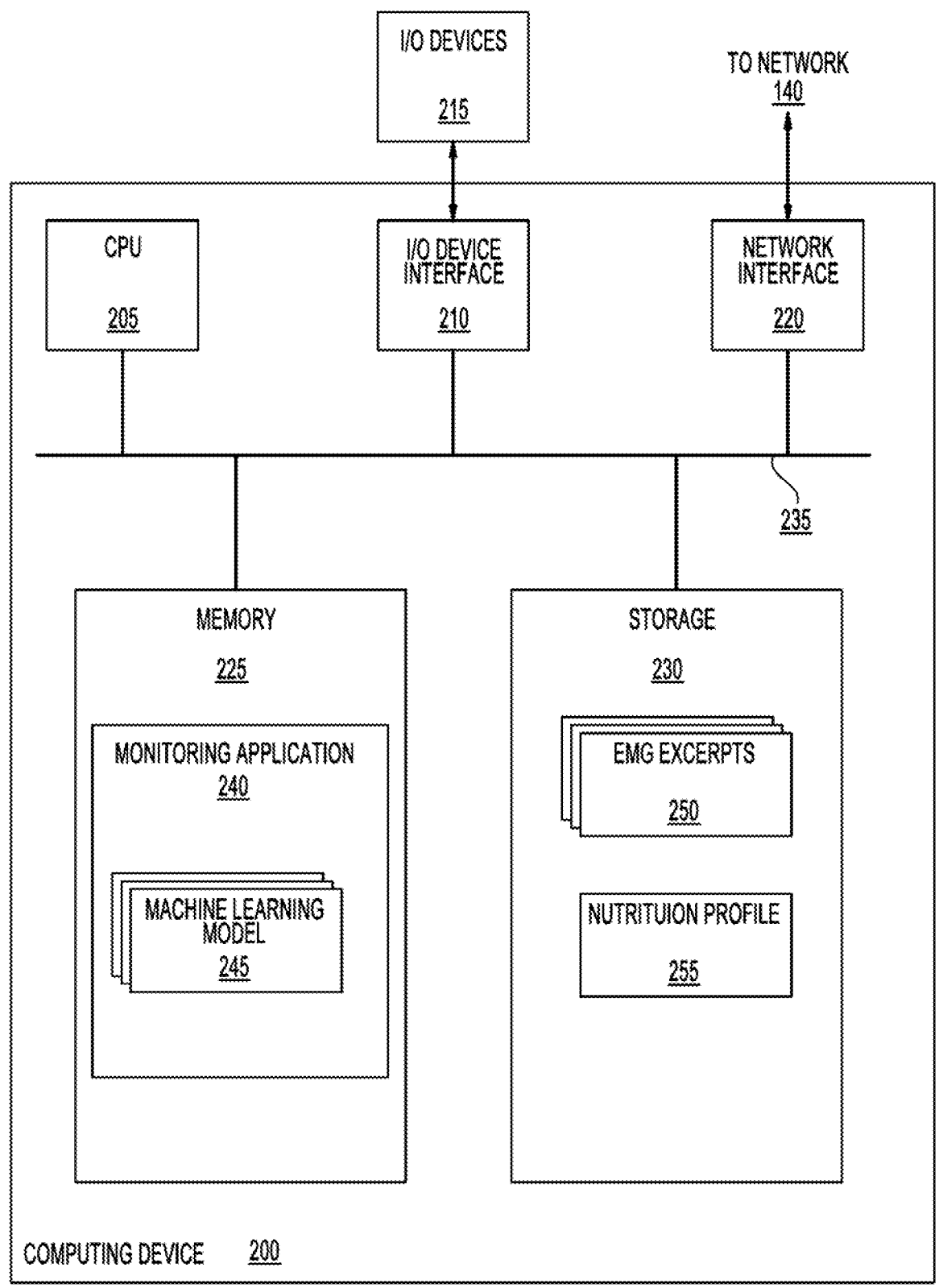
FIG. 2 is a block diagram illustrating a computing device capable of implementing one embodiment of the present disclosure.

FIG. 2 is a block diagram illustrating a Computing Device 200 capable of implementing one embodiment of the present disclosure. For example, in an embodiment the Computing Device 200 is a mobile telephone. As illustrated, Computing Device 200 includes a CPU 205, an I/O Device Interface 210, a Network Interface 220, a Memory 225, and a Storage 230, each connected via a bus or interconnect 235. In an embodiment, the I/O Device Interface 210 is used to connect I/O devices (e.g., keyboard, display and mouse devices) to the Computing Device 200.

The CPU 205 is configured to retrieve and execute programming instructions stored in the memory 225 and storage 230. Similarly, the CPU 205 is configured to store and retrieve application data residing in the memory 225 and storage 230. The interconnect 235 is configured to move data, such as programming instructions and application data, between the CPU 205, storage unit 230, network interface 220, memory 225, and I/O Device Interface 110. The CPU 205 is included to be representative of a single CPU, multiple CPUs, a single CPU having multiple processing cores, and the like. Memory 225 is generally included to be representative of a random access memory. The network interface 220 is configured to transmit data via the communications network 140. Although shown as a single unit, the storage 230 may be a combination of fixed and/or removable storage devices, such as fixed disc drives, removable memory cards, optical storage, SSD or flash memory devices, network attached storage (NAS), or connections to storage area-network (SAN) devices.

In an embodiment, Network 140 is a personal area network, such as a Bluetooth connection. In some embodiments, Network 140 is a local area network or wide area network, such as the Internet. As illustrated, Memory 225 contains a Monitoring Application 240, which includes multiple Machine Learning Models 245. Storage 230 includes multiple EMG Excerpts 250, and a Nutrition Profile 255. Of course, each of these could reside in Memory 225, in Storage 230, or any other suitable location. As will be discussed below in more detail, the illustrated Monitoring Application 240 is generally configured to receive EMG data from a wearable device, process the data using one or more Machine Learning Models 245, and determine whether the user is currently consuming food or beverages. In an embodiment, received EMG data is also stored as EMG Excerpts 250 for later use.

Upon determining that the user is consuming food, Computing Device 200 transmits a control signal using Network Interface 220, instructing a wearable device to capture one or more images. When the images are received, Monitoring Application determines the nutritional content of the food or beverage in the captured images, as will be discussed in more detail below. In an embodiment, upon determining the nutritional content of the food, Monitoring Application 240 updates the user's Nutrition Profile 255 to track the consumption of food and beverages.

The Machine Learning Model 245 can be trained in various ways. Generally, the Machine Learning Models 245 are trained by providing EMG data from one or more users, along with an indication of whether or not the respective user is currently consuming a food or drink. After being trained, the model can be provided with new EMG data, and can generate an indication as to whether the user is eating or drinking. In an embodiment, a single Machine Learning Model 245 is trained to identify both eating and drinking. In some embodiments, however, there is a first Machine Learning Model 245 trained to detect eating, and a second Machine Learning Model 245 trained to detect drinking. Similarly, in some embodiments, several Machine Learning Models 245 are trained to detect consumption of various types of food. For example, a first Machine Learning Model 245 may be trained to detect consumption of soup, while another is trained to detect consumption of other food.

In some embodiments, EMG data is provided to the one or more Machine Learning Models 245 without any processing. In other embodiments, the data may be provided to the Machine Learning Model 245 only after one or more pre-processing steps are undertaken. For example, the EMG data may be processed to smooth the data, to remove outliers (unexpectedly high peaks), and the like. In an embodiment, various pre-processing techniques can improve the accuracy of the Machine Learning Models 245 by reducing false positives (e.g., when the system determines the user is eating when, in fact, he is not) as well as false negatives (e.g., when the system determines the user is not eating when, in fact, he is).

In an embodiment, the one or more Machine Learning Models 245 are pre-trained before use by a user. That is, in an embodiment, an administrator or other individual trains the models by providing them with EMG data and an indication of whether the EMG data was recovered from a user who was consuming food or beverages. The models may then be provided users for actual use. In another embodiment, the user may train one or more Machine Learning Models 245 using his own EMG data. In such an embodiment, a user can use the wearable device throughout the day, and provide an indication to the wearable device and/or the Computing Device 200 whenever he is eating or drinking. For example, in an embodiment, the user presses a button on the wearable device or Computing Device 200 to indicate that he is eating.

In some embodiments, the Machine Learning Models 245 are initially trained using generic data for a number of different users, and refined using each user's specific data. That is, an administrator may collect EMG data from any number of people and use it to train one or more Machine Learning Models 245, which are then provided to each user of a wearable device. As each user begins to use the wearable device, the models may be refined using data unique to the user. In this way, the Machine Learning Models 245 can be made more accurate by being refined and specifically tailored towards each individual user.

In an embodiment, in addition to providing the indication as to whether the user is eating, the models can be trained by providing an indication as to what the user is consuming. For example, a user may use Computing Device 245 to indicate that she is drinking a beverage, eating soup, or chewing a sandwich. Monitoring Application 245 may then use this information to train or refine the Machine Learning Models 245 to identify not only that the user is consuming something, but also what food or drink the user is likely consuming. In an embodiment, this improves the accuracy of the Machine Learning Models 245 and facilitates the process of monitoring consumption.

Figure 3:
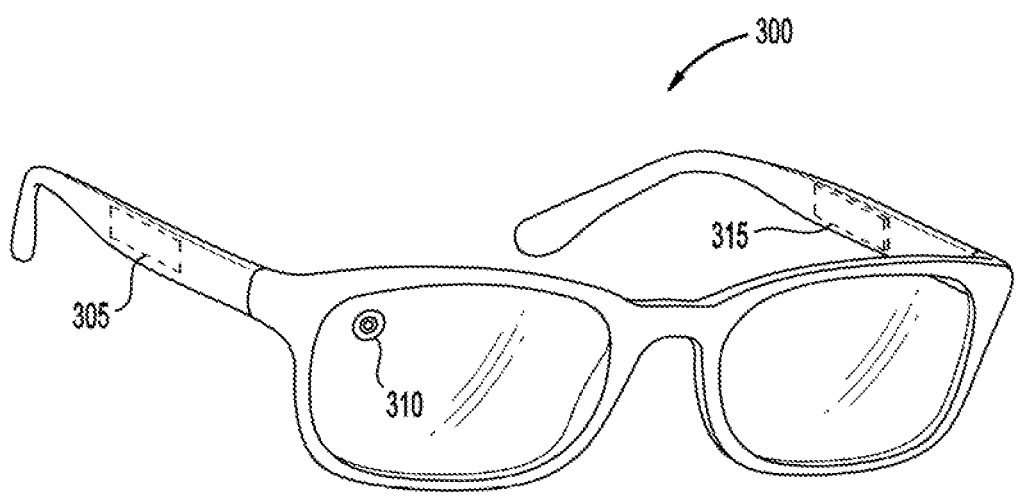
FIG. 3 illustrates an eyeglass-based wearable device, according to one embodiment of the present disclosure.

FIG. 3 illustrates an eyeglass-based Wearable Device 300, according to one embodiment of the present disclosure. As illustrated, Wearable Device 300 includes an EMG Sensor 315, a Camera 310, and a Processor 305. In the illustrated embodiment, Wearable Device 300 includes a single EMG Sensor 315, which is situated on one arm of the Wearable Device 300. For example, EMG Sensor 315 may be embedded in the arm, on the surface of the arm, and the like. In some embodiments, however, there may be multiple EMG Sensors 315. For example, in one embodiment, there are two EMG Sensors 315, one on each arm of the Wearable Device 300. This allows for detecting EMG data from both sides of the user's head. As used herein, EMG data refers to the electrical activity produced by skeletal muscles when moving. In an embodiment, the EMG Sensor(s) 315 are configured to detect EMG data originating in muscles that control the user's mandible or jaw. For example, in an embodiment, the monitored muscles can include the masseter, temporalis, medial pterygoid, and/or lateral pterygoid. In some embodiments, other muscles may be monitored, including the sphenomandibularis, the hyoid, the trapezius, and/or the sternomastoid.

In the illustrated embodiment, Processor 305 is located in the other arm of Wearable Device 300, but of course may be located in any suitable location on or in Wearable Device 300. Although not depicted, Wearable Device 300 may also include one or more energy sources, such as a battery, as well as a network interface for transmitting and receiving data. As illustrated, the Camera 310 is located on the lens of the Wearable Device 300. In some embodiments, however, the Camera 310 (or other imaging sensor) may be located in any other suitable location on Wearable Device 300, for example, on the bridge of the Wearable Device 300 that connects the lenses together or any other suitable location.

Figure 4:
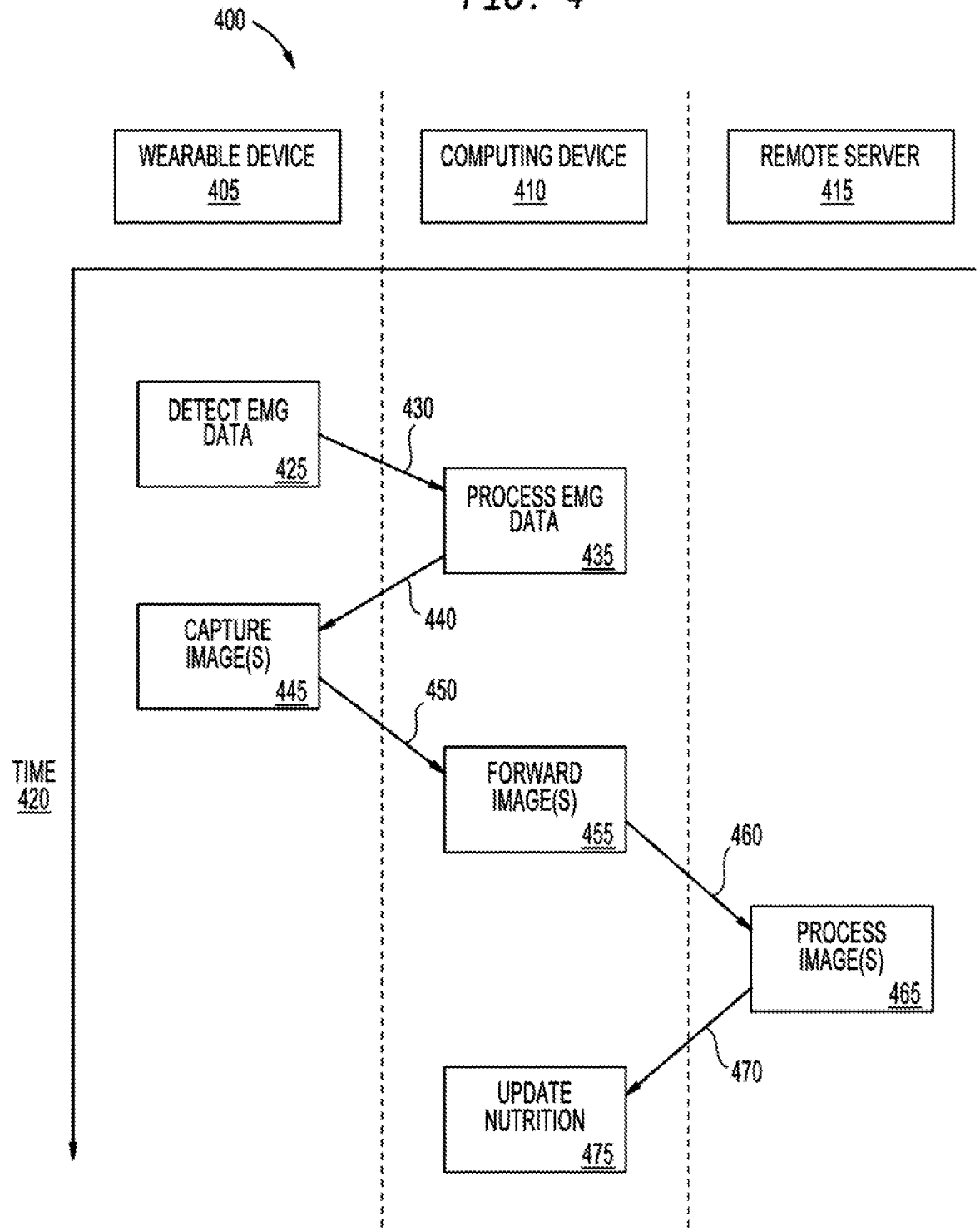
FIG. 4 is a diagram illustrating a workflow for monitoring eating habits, according to one embodiment of the present disclosure.

FIG. 4 is a diagram illustrating a workflow 400 for monitoring eating habits, according to one embodiment of the present disclosure. As illustrated, the workflow 400 takes place across three different devices, Wearable Device 405, Computing Device 410, and Remote Server 415. Of course, in some embodiments, the workflow 400 may occur entirely within Wearable Device 405, or between Wearable Device 405 and Computing Device 410. As illustrated, the various operations and processes occur as time progresses over Time 420 axis. The workflow 400 begins at block 425, where Wearable Device 405 detects EMG data. For example, as discussed above, one or more EMG Sensors may detect jaw movement of the user. As illustrated by arrow 430, the EMG data is transmitted to Computing Device 410. For example, the EMG data may be transmitted over a personal area network, such as Bluetooth, over a local area network, or a wide area network, such as the Internet.

In an embodiment, the EMG data may be transmitted as a stream of data, e.g., representing the movement of the user's jaw at any given moment. In some embodiments, the EMG data is transmitted as a series of blocks of data. For example, the blocks of EMG data may be delineated into fixed periods of time. In some embodiments, the EMG data is delineated into blocks based on the content of the data. For example, a break between two blocks may occur when the activity subsides, for example, because the user is not moving his mouth. In some embodiments, all detected EMG data is transmitted to Computing Device 410. In other embodiments, however, only EMG data that exceeds a predefined threshold is transmitted. For example, if the detected peaks in the EMG data are below a predefined threshold, or occur infrequently, the EMG data may be discarded and not transmitted.

At block 435, Computing Device 410 processes the EMG data to determine whether the user is actively consuming food or beverages. For example, in an embodiment, Computing Device 410 processes the data using one or more trained machine learning models, as discussed above. In an embodiment utilizing a single machine learning model to identify both eating and drinking, the data is provided to the single model. In an embodiment utilizing multiple machine learning models, the received EMG data may be processed by some or all of the models to determine whether the user is eating or drinking. For example, in an embodiment with one model trained to identify eating and another trained to identify drinking, the EMG data may be provided to both, and the output from both models is considered. If no consumption is detected, the workflow terminates.

If consumption is detected, however, Computing Device 410 transmits a control signal to Wearable Device 405, which is illustrated by arrow 440. For example, the control signal may be transmitted over a personal area network, a local area network, or a wide area network. Upon receiving the control signal, Wearable Device 405 captures one or more images at block 445. For example, as illustrated in FIG. 3, an imaging sensor on the front of an eyeglass-based Wearable Device 405 will capture images of whatever the user is looking at, which may include food being consumed.

In an embodiment, Wearable Device 405, Computing Device 410, or both may output an indication that one or more images are being captured. For example, Wearable Device 405 or Computing Device 410 may vibrate, enable a light, display something on a screen, emit a sound, and the like. In such an embodiment, the user knows whether the Wearable Device 405 is currently taking pictures, which helps to ensure the privacy of the user. In some embodiments, if the Wearable Device 405 or Computing Device 410 indicate that images are being captured, the user can indicate that she is not, in fact, consuming any food or drink. Such an indication could be provided by, for example, a button or touch surface on Wearable Device 405 or Computing Device 410, through a verbal command, and the like. Upon receiving this indication, the one or more machine learning models can be refined to correct for the false positive. Similarly, if no images are being captured despite the fact that the user is currently consuming food, the user may provide an indication that he or she is consuming food or beverages, in order to further refine the models to correct for the false negative.

As illustrated by arrow 450, the one or more images are then transmitted to Computing Device 410. At block 455, Computing Device 410 forwards the images to a Remote Server 415. For example, in an embodiment, Remote Server 415 is a cloud server hosting one or more components that can be used to process images. The processing may be achieved using, for example, neural networks, recurrent neural networks, machine learning, and the like. As represented by block 465, Remote Server 415 processes the one or more images to determine what type(s) of food or beverage are present in the image. Further, in an embodiment, Remote Server 415 also determines nutritional content of the identified food or beverage, for example, by reference to a database. In another embodiment, Remote Server 415 identifies the food or drink, and Computing Device 410 uses a database or other data structure to determine nutritional content of that food or drink.

In an embodiment, before transmitting the one or more images to the Remote Server 415, the data is anonymized in a number of ways. For example, any metadata regarding the user's identity, location, and the like can be purged such that there is no identifying data in the images. Advantageously, this protects the privacy of the user. Additionally, in some embodiments, a delay elapses before the images are transmitted to Remote Server 415, in order to give the user time to cancel the transmission. For example, if any classified, sensitive, or embarrassing content may be visible in one or more of the images, the user may want to prevent it from being transmitted to the Remote Server 415. In an embodiment, this delay may be user definable. For example, a user may instruct the Computing Device 410 to collect images throughout the day, but only transmit them to Remote Server 415 for processing once a day, once every hour, every five minutes, after a ten second delay, and the like. Further, in some embodiments, the images are transmitted to Remote Server 415 only upon approval of the user.

As illustrated by arrow 470, Remote Server 415 transmits the determined identity of the food or beverage (along with, in some embodiments, the nutritional information) to Computing Device 410. In an embodiment, if no food or beverage is detected in a received image, Remote Server 415 transmits an indication to Computing Device 410. Upon receiving this indication, Computing Device 410 can refine the machine learning models, e.g., because they must have yielded a false positive. Upon receiving the identification and/or nutritional information, Computing Device 410 updates a nutrition profile of the user. In an embodiment, the nutrition profile contains information about food and beverages consumed by the user. For example, the profile may contain a number of meals or snacks eaten, the number of calories consumed, the total fats and sugars consumed, and the like.

Although the illustrated workflow 400 includes three devices, Wearable Device 405, Computing Device 410, and Remote Server 415, some embodiments utilize only some of the devices. For example, in the illustrated embodiment, Computing Device 410 transmits the images to Remote Server 415 because Computing Device lacks the processing power, storage, or other computational resources to efficiently process the images. In another embodiment, however, Computing Device 410 processes the images locally, and Remote Server 415 is not involved. Similarly, in the illustrated embodiment, Wearable Device 405 transmits the EMG data to Computing Device 410 because the Wearable Device 405 lacks the computational resources to process it. In some embodiments, however, the EMG data can be processed using machine learning by Wearable Device 405, and it is not transmitted to Computing Device 410. Additionally, in some embodiments, the images are also processed by Wearable Device 405, and there are no other devices involved in the workflow.

Figure 5:
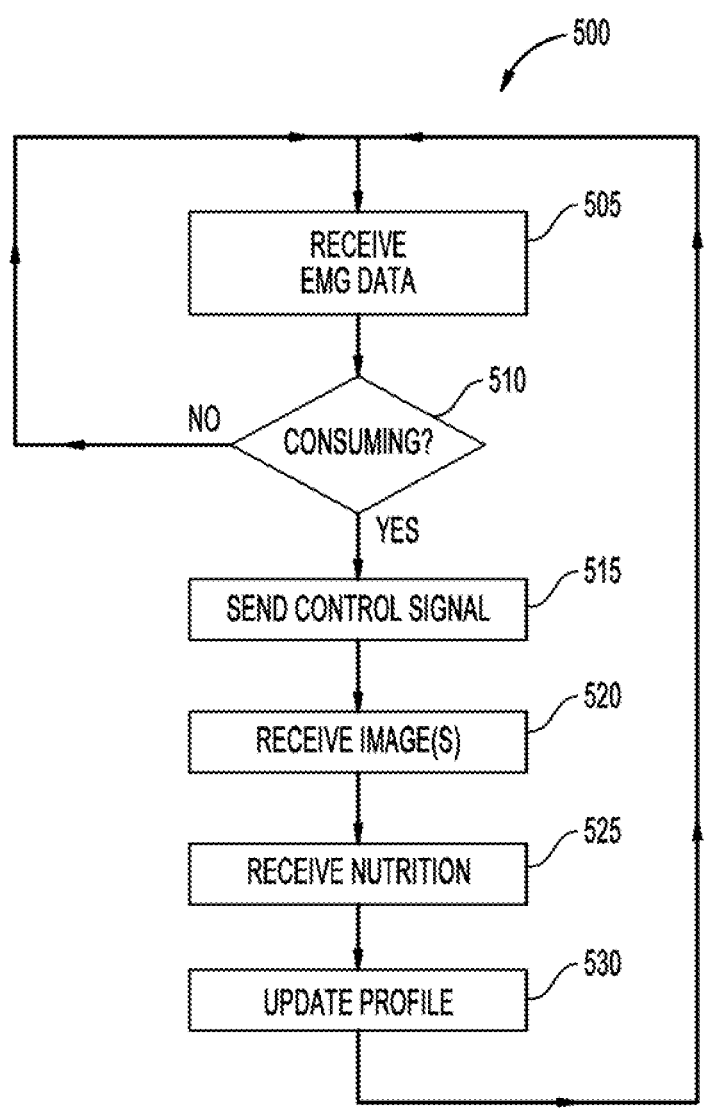
FIG. 5 is flow diagram illustrating a workflow for monitoring eating habits, according to one embodiment of the present disclosure.

FIG. 5 is flow diagram illustrating a workflow 500 for monitoring eating habits, according to one embodiment of the present disclosure. The workflow begins at block 505, where Computing Device 200 receives EMG data. At block 510, Computing Device 200 processes the data to determine whether the user is consuming food or beverages. For example, as discussed above, Computing Device 200 may use one or more machine learning models. If it is determined that the user is not currently consuming food or drink, the workflow 500 returns to block 505 to receive additional EMG data. If, however, it is determined that the user is currently eating or drinking, the workflow progresses to block 515, where Computing Device 200 transmits a control signal to the wearable device. At block 520, one or more images are received by Computing Device 200.

At block 525, Computing Device 200 determines the nutritional content of the food or drink being consumed. For example, as discussed above, Computing Device 200 may transmit the one or more images to a remote server for processing, or may process them locally. At block 530, Computing Device 200 updates the user's profile, and the workflow returns to block 505 to continue monitoring for EMG data.

In an embodiment, in addition to processing the one or more images with a machine learning model to identify the type of food, the system is also configured to determine how much food is being consumed. In some embodiments, this determination is made based on the detected number of bites, along with a predefined average bite size. For example, the bite size could be defined by an administrator, or by the specific user. Further, in some embodiments, the bite size may vary according to the type of food consumed. In such an embodiment, once the food has been identified, the appropriate predefined bite size can be used to determine an amount of food consumed based on the number of bites taken. In an embodiment, the number of bites taken is determined based on the EMG data, for example, based on the length of time the user ate, the number of peaks in the data, and the like.

In a related embodiment, the EMG data may be analyzed, for example by one or more machine learning models, to determine an amount of food consumed without reference to an average bite size. In various embodiments, this may be based on the number of bites or chewing motions, the length of time the motion continued, the amplitude of the peaks in the EMG data, and the like. Thus, for example, the machine learning model may be trained to recognize larger peaks in the EMG data or prolonged chewing before swallowing or taking a break in chewing. Additionally, in some embodiments, the images may be further processed to determine an amount of food consumed. For example, the images may be processed by one or more machine learning models to estimate an initial portion size. Subsequently, the images can be processed to determine how much of the portion remains, or how much food has been consumed. In this way, the system can determine not only what type of food was consumed, but also how much of the food has been consumed, which increases the accuracy of the nutrition profile.

FIG. 6 is a flow diagram illustrating a method 600 for monitoring eating habits, according to one embodiment of the present disclosure. At block 605, a wearable device collects EMG data via one or more electromyography sensors. The method 600 continues at block 610, where the wearable device transmits the EMG data to a computing device. At block 615, the wearable device receives, from the computing device, a control signal to capture one or more images via an imaging sensor. The method 600 continues at block 620, where the wearable device captures, via the imaging sensor, one or more images. Finally, at block 625, the wearable device transmits, to the computing device, the one or more images.

FIG. 7 is a flow diagram illustrating a method 700 for monitoring eating habits, according to one embodiment of the present disclosure. At block 705, a computing device receives, from a wearable device, EMG data. At block 710, the computing device processes the EMG data as an input to a trained machine learning model to determine that the received EMG data matches a predefined pattern of EMG data corresponding to a jaw movement of a user wearing the wearable device. The method 700 continues at block 715, where the computing device transmits, to the wearable device, a control signal to capture one or more images via an imaging sensor. At block 720, the computing device receives, from the wearable device, the one or more images, and at block 725, the computing device determines nutritional content of the food or beverage using the one or more images.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

In the following, reference is made to embodiments presented in this disclosure. However, the scope of the present disclosure is not limited to specific described embodiments. Instead, any combination of the following features and elements, whether related to different embodiments or not, is contemplated to implement and practice contemplated embodiments. Furthermore, although embodiments disclosed herein may achieve advantages over other possible solutions or over the prior art, whether or not a particular advantage is achieved by a given embodiment is not limiting of the scope of the present disclosure. Thus, the following aspects, features, embodiments and advantages are merely illustrative and are not considered elements or limitations of the appended claims except where explicitly recited in a claim(s). Likewise, reference to "the invention" shall not be construed as a generalization of any inventive subject matter disclosed herein and shall not be considered to be an element or limitation of the appended claims except where explicitly recited in a claim(s).

Aspects of the present invention may take the form of an entirely hardware embodiment, an entirely software embodiment (including firmware, resident software, microcode, etc.) or an embodiment combining software and hardware aspects that may all generally be referred to herein as a "circuit," "module" or "system."

The present invention may be a system, a method, and/or a computer program product. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

Embodiments of the invention may be provided to end users through a cloud computing infrastructure. Cloud computing generally refers to the provision of scalable computing resources as a service over a network. More formally, cloud computing may be defined as a computing capability that provides an abstraction between the computing resource and its underlying technical architecture (e.g., servers, storage, networks), enabling convenient, on-demand network access to a shared pool of configurable computing resources that can be rapidly provisioned and released with minimal management effort or service provider interaction. Thus, cloud computing allows a user to access virtual computing resources (e.g., storage, data, applications, and even complete virtualized computing systems) in "the cloud," without regard for the underlying physical systems (or locations of those systems) used to provide the computing resources.

Typically, cloud computing resources are provided to a user on a pay-per-use basis, where users are charged only for the computing resources actually used (e.g. an amount of storage space consumed by a user or a number of virtualized systems instantiated by the user). A user can access any of the resources that reside in the cloud at any time, and from anywhere across the Internet. In context of the present invention, a user may access applications (e.g., machine learning models) or related data available in the cloud. For example, the Monitoring Application 240 or image processing component could execute on a computing system in the cloud and process EMG data and/or images. In such a case, the image processing component or monitoring application could identify consumption of food, determine food type and nutrition information, and store the nutrition profile at a storage location in the cloud. Doing so allows a user to access this information from any computing system attached to a network connected to the cloud (e.g., the Internet).

While the foregoing is directed to embodiments of the present invention, other and further embodiments of the invention may be devised without departing from the basic scope thereof, and the scope thereof is determined by the claims that follow.

What is claimed is:

1. A system comprising:
  a computing device, comprising:
    a processor; and
    a memory containing a machine learning model and computer program code that, when executed, performs an operation; and
  a wearable device, comprising:
    an imaging sensor;
    one or more electromyography (EMG) sensors; and
    a processing unit;
    wherein the processing unit of the wearable device is configured to:

collect EMG data collected via the one or more electromyography sensors of the wearable device;
compare the EMG data to one or more thresholds;
upon determining that the EMG data satisfies the one or more predefined thresholds, transmit the EMG data to the computing device;
receive, from the computing device, a control signal to capture one or more images via the imaging sensor;
capture, via the imaging sensor, one or more images; and
transmit, to the computing device, the one or more images; and
wherein the operation performed by execution of the computer program code of the computing device comprises:
receiving a delay parameter, wherein the delay parameter defines when captured images are processed;
receiving, from the wearable device, the EMG data;
processing the EMG data as an input to a trained machine learning model to determine that the received EMG data matches a predefined pattern of EMG data corresponding to a jaw movement of a user wearing the wearable device;
transmitting, to the wearable device, the control signal to capture one or more images via the imaging sensor;
receiving, from the wearable device, the one or more images;
refraining from processing the one or more images until the delay parameter is satisfied; and
upon determining that the delay parameter is satisfied, determining nutritional content of the food or beverage using the one or more images.

2. The system of claim 1, wherein the wearable device is an eyeglass-based device.

3. The system of claim 2, wherein the eyeglass-based device comprises a first EMG sensor positioned on a first arm of the eyeglass-based device, and a second EMG sensor positioned on a second arm of the eyeglass-based device.

4. The system of claim 1, wherein the computing device is a mobile telephone.

5. The system of claim 1, wherein the first machine learning model was initially trained using EMG data corresponding to at least one second user.

6. The system of claim 5, wherein the first machine learning model is refined using EMG data corresponding to the first user.

7. The system of claim 1, wherein determining nutritional content of the food or beverage comprises transmitting the one or more images to a remote server for processing using a second machine learning model.

8. The system of claim 1, wherein the operation performed by execution of the computer program code of the computing device further comprises updating a nutritional profile corresponding to the first user upon determining the nutritional content of the food or beverage.

9. A method comprising:
receiving a delay parameter, wherein the delay parameter defines when captured images are processed;
receiving electromyography (EMG) data from a wearable device, wherein the EMG data represents jaw movement of a first user wearing the wearable device;
processing the received EMG data using a first machine learning model to determine that the user is consuming food;
transmitting a control signal to the wearable device, wherein the control signal instructs the wearable device to capture one or more images using an imaging sensor of the wearable device;
receiving the one or more images from the wearable device;
refraining from processing the one or more images until the delay parameter is satisfied; and
upon determining that the delay parameter is satisfied, determining nutritional content of the food using the one or more images.

10. The method of claim 9, wherein the wearable device is an eyeglass-based device.

11. The method of claim 10, wherein the eyeglass-based device comprises a first EMG sensor positioned on a first arm of the eyeglass-based device, and a second EMG sensor positioned on a second arm of the eyeglass-based device.

12. The method of claim 9, wherein the first machine learning model was initially trained using EMG data corresponding to at least one second user.

13. The method of claim 12, wherein the first machine learning model is refined using EMG data corresponding to the first user.

14. The method of claim 9, wherein determining the nutritional content of the food or beverage comprises:
transmitting the one or more images to a remote server for processing using a second machine learning model; and
receiving the nutritional content of the food or beverage.

15. The method of claim 9, the method further comprising updating a nutritional profile corresponding to the first user upon determining the nutritional content of the food or beverage.

16. A computer-readable storage medium having computer-readable program code embodied therewith, the computer-readable program code executable by one or more computer processors to perform an operation comprising:
receiving a delay parameter, wherein the delay parameter defines when captured images are processed;
receiving, from a wearable device, electromyography (EMG) data about jaw movement of a user;
determining that the user is consuming food or beverages by processing the EMG data using a first trained machine learning model;
transmitting, to the wearable device, an instruction to capture one or more images;
receiving, from the wearable device, the one or more images;
refraining from processing the one or more images until the delay parameter is satisfied; and
upon determining that the delay parameter is satisfied, determining nutritional content of the food or beverage using the one or more images.

17. The computer-readable storage medium of claim 16, wherein the wearable device is an eyeglass-based device comprising a first EMG sensor positioned on a first arm of the eyeglass-based device, and a second EMG sensor positioned on a second arm of the eyeglass-based device.

18. The computer-readable storage medium of claim 16, wherein the first machine learning model was initially trained using EMG data corresponding to at least one second user, and wherein the first machine learning model is refined using EMG data corresponding to the first user.

19. The computer-readable storage medium of claim 16, wherein determining the nutritional content of the food or beverage comprises:

transmitting the one or more images to a remote server for processing using a second machine learning model; and receiving the nutritional content of the food or beverage.

20. The computer-readable storage medium of claim 16, the operation further comprising updating a nutritional profile corresponding to the first user upon determining the nutritional content of the food or beverage.

* * * * *